United States Patent [19]

Francis

[11] 4,216,211

[45] Aug. 5, 1980

[54] THERAPEUTIC COMPOSITION

[75] Inventor: Marion D. Francis, Cincinnati, Ohio

[73] Assignee: The Procter & Gamble Company, Cincinnati, Ohio

[21] Appl. No.: 847,190

[22] Filed: Oct. 31, 1977

Related U.S. Application Data

[62] Division of Ser. No. 685,969, May 13, 1976, Pat. No. 4,067,971.

[51] Int. Cl.² .............................................. A61K 31/66
[52] U.S. Cl. ................................................... 424/204
[58] Field of Search ........................................ 424/204

[56] References Cited

U.S. PATENT DOCUMENTS

| | | | |
|---|---|---|---|
| 3,641,246 | 2/1972 | Francis | 424/204 |
| 3,662,066 | 5/1972 | Francis | 424/204 |
| 3,678,164 | 7/1972 | Francis | 424/204 |
| 3,683,080 | 8/1972 | Francis | 424/204 |
| 3,795,581 | 5/1974 | Deindoerfer et al. | 424/331 |

*Primary Examiner*—Stanley J. Friedman
*Attorney, Agent, or Firm*—Michael J. Roth; Jerry J. Yetter; Richard C. Witte

[57] ABSTRACT

Phosphonate compounds are employed in the treatment of hypoxias and ischemic tissue diseases.

5 Claims, No Drawings

THERAPEUTIC COMPOSITION

This is a division, of application Ser. No. 685,969, filed May 13, 1976, now U.S. Pat. No. 4,067,971.

BACKGROUND OF THE INVENTION

The present invention relates to the prophylactic and therapeutic treatment of hypoxia and ischemic tissue disease. Phosphonate compounds are administered therapeutically to protect a tissue or organ against degeneration, necrosis and fibrosis following blockage of the blood supply to that tissue or organ. In the alternative, phosphonate compounds are administered prophylactically for the prevention of tissue or organ necrosis caused by ischemia of that tissue or organ, whatever the primary cause or etiology.

Hypoxia is a term used to connote an inadequate supply of oxygen available to, or utilized by, tissue, without regard to cause or degree. Hypoxia can be the result of disease states, as in the case of the various anemias, or can result from a low oxygen tension in the blood, as in the case of high altitude "sickness".

Ischemia is a term used to connote, in an overall way, localized tissue anemia due to the obstruction of the flow of arterial blood or to vasoconstriction. Obstruction or scenosis of a blood vessel to a tissue or organ results in tissue damage, progressive degeneration, and ultimate necrosis and fibrosis of that tissue or organ.

Ischemia can be the result of either the precipitous stoppage of arterial blood flow, or the more gradual, but usually progressive, diminution of flow. For example, ischemic heart disease can be caused by coronary occlusion (myocardial infarction) or by a more generalized coronary artery insufficiency. Cerebral ischemias and other tissue ischemias such as renal and bone infarcts are well-recognized disease states which are difficult to treat. Another disease state of this general type involves the ischemia of the peripheral tissues secondary to diabetes mellitus, and it is this type of ischemic disease which can result in retinopathies, loss of renal function, neuropathies, or nacrosis and amputation of limbs in extreme cases.

By the present invention, certain phosphonate compounds, especially diphosphonates, are used in the treatment of hypoxia and ischemic tissue diseases. Such diseases include: myocardial infarction; senility; microangiopathies, including retinopathy, neuropathy, and chronic renal failure; pernicious anemia; iron-deficiency anemia; allergic reactions such as immediate and delayed hypersensitivity; and chronic hypoxic lung diseases such as emphysema, asthma, hyaline-membrane disorders, chronic bronchitis and cor pulmonale.

DISCUSSION OF RELATED REFERENCES

The phosphonate compounds used in the practice of this invention are reported in the literature as being useful in the treatment of anomalous mobilization and deposition of calcium phosphate salts (bone mineral) in humans and other animals. See especially the U.S. Pat. Nos. of M. D. Francis: 3,678,164, granted July 18, 1972; 3,662,066, granted May 9, 1972; 3,553,314, granted Jan. 5, 1971; 3,553,315, granted Jan. 5, 1971; 3,584,124, granted June 8, 1971; 3,584,125, granted June 8, 1971; and 3,641,246, granted Feb. 8, 1972.

Attention is directed to U.S. Pat. No. 3,683,080. to M. D. Francis, issued Aug. 8, 1972, wherein the problem of calcification of soft tissues is noted (Col. 1, lines 55, et seq.). In this disclosure, it is noted that atherosclerosis is a condition which involves degeneration and proliferate change in the intima of arteries which results in fibrous, lipid phaques. If such plaques calcify, or if the inner walls of the arteries accumulate plaque and calcify, the resulting condition is commonly referred to as arteriosclerosis. The phosphonates are taught to be a means for inhibiting such anomalous calcification. See also, German DT 2360-798 (June 26, 1975); German DT 2343-146 (March 6, 1975); Belgian BE 822-929 Dec. 6, 1973) and other patents cited hereafter in this specification which mention the use of phosphonates to treat anomalous calcification and arteriosclerosis.

In contrast with the prior art disclosures of the use of phosphonate materials to prevent the formation of anomalous bone mineral deposits in hard and soft tissues, including blood vessles, the present invention is based on the new discovery that the phosphonates afford a treatment for tissues and organs subject to hypoxia, tissue damage and ultimate necrosis and fibrosis as a result of "oxygen starvation", whatever the etiology.

As demonstrated by the ANIMAL STUDIES described hereinafter, the phosphonate compounds diminish the severity of organ infarcts caused by blockage (ligation) of blood vessels. Since, in these studies the vessels were artificially ligated, the desirable physiological effects of the phosphonates are not ascribable to removal of calcium phosphate deposits in the vessels, but to a heretofore unsuspected benefit afforded by phosphonate compounds.

As demonstrated by the in vitro BLOOD STUDIES described hereinafter, the phosphonate compounds (especially ethane-1-hydroxy-1,1-diphosphonate) cause an increase in the rate of deoxygenation of whole blood. The blood can thus release oxygen to tissues starved for oxygen in a more efficient and effective manner.

SUMMARY OF THE INVENTION

The present invention encompasses a process for treating (alleviating) or preventing hypoxia in an animal, especially humans, comprising administering to said animal in need of such treatment or prevention sufficient phosphonate compound of the type disclosed hereinafter to alleviate or prevent said hypoxia.

The prevent invention also encompasses a process for increasing the rate of deoxygenation of blood in animals, especially humans, comprising administering to said animal in need of such treatment sufficient phosphonate compound to increase the rate of release of oxygen from blood on demand or need by tissues.

The present invention also encompasses a process for treating or preventing tissue or organ damage in an animal, especially humans, caused by ischemia of that tissue or organ, comprising administering to said animal in need of such treatment or prevention sufficient phosphonate compound to treat or prevent said tissue or organ damage, i.e., tissue infarct.

The present invention also encompasses a process for protecting a tissue or organ in an animal, especially humans, against subsequent degeneration, necrosis and fibrosis following infarction of that tissue or organ, comprising administering to said animal suffering from said infarct sufficient phosphonate compound to protect said tissue or organ against said subsequent degeneration, necrosis and fibrosis.

The present invention also encompasses a process for increasing the level of 2,3-diphosphoglycerate (2,3-DPG) in the blood of animals, especially humans, having need for such treatment, comprising administering to said animal sufficient phosphonate compound to increase the blood level of said 2,3-DPG.

By "administration" of the phosphonate compounds herein is meant systemic use, as by injection (especially parenterally), intravenous infusion, oral administration, or aspiration thereof.

DETAILED DESCRIPTION OF THE INVENTION

Various conditions associated with hypoxia such as exposure to high altitude, anemias, cardiac decompensation, chronic lung disease, chronic allergies, and the like, are prevalent medical problems. It has been determined that the natural body response to such hypoxias is to increase the level of 2,3-diphosphoglycerate (2,3-DPG) in the blood. 2,3-DPG is known to be a regulator of the affinity of hemoglobin for oxygen. The more 2,3-DPG in the blood, the more easily oxygen is released from hemoglobin into the tissues. In the hypoxic state, the decreased capacity of blood to carry oxygen is at least partially compensated for by the improved release of oxygen in the tissues. See Greenwald, I., *J. Biol. Chem.* 63:339 (1925); Benesch, R. and Benesch, R. E., *Biochem. Biophys. Res. Comm.* 26:162 (1967); and Chanutin, A. and Curnish, R. R., *Archs. Biochem. Biophys.* 121:96 (1967).

In light of the foregoing, it will be appreciated that any agent which increases the 2,3-DPG level in the blood or otherwise increases the rate of deoxygenation of blood to provide more efficient delivery of oxygen to tissues merits careful consideration as a treatment for hypoxia. Indeed, various androgens have been shown to increase the 2,3-DPG level in the blood and have been used successfully to treat hypoxias associated with bone marrow failure and related clinical conditions associated with renal failure. Unfortunately, androgens cannot be used with pregnant females and precautions must be taken when they are administered to patients with cardiac, renal or hepatic diseases.

The phosphonates herein (especially the diphosphonates) provide an alternative to androgens in the treatment of hypoxias in that they, too, have now been found to increase the rate of deoxygenation of blood and appear to increase the level of 2,3-DPG in the blood in some subjects.

Tissue and organ hypoxia due to decreased blood flow is characteristic of the ischemic state. Ischemia of tissues and organs caused by a variety of disease states results in the progressive degeneration of said tissues or organs. For the most part, the ischemic condition may be considereed to be the inevitable result of genetic problems or diseases states affecting the body's vascular system. For example, diabetes mellitus is a metabolic disorder which, by itself, rarely leads to death. Instead, diabetes almost always results in other complications which are debilitating or fatal to the sufferer. One of the most common complications in the diabetic patient is vascular occlusion and death by ensuing heart attack (myocardial infarction) or other forms of vascular disease (generally, ischemic necrosis, especially of the kidneys).

Athero-arteriosclerosis and related vascular diseases comprise perhaps the most prevalent degenerative change in the human cardio-vascular system. The etiology of these so-called "diseases of aging" is still unknown and has been the subject of controversy among medical scientists for over a century. In any event, it is recognized that prolonged and progressive loss of blood flow to body tissues and concomitant oxygen "starvation" must, ultimately, result in progressive tissue degeneration.

As with any hypoxia, in the ischemic state the decreased flow through the body's vascular system can be compensated for by a more effective exchange of oxygen at the site for release in the tissues and organs. Accordingly, administration of a drug such as the phosphonates herein which increases the efficiency of $O_2$ release per pass of blood volume is indicated for the treatment of tissue and organ ischemia.

It will be appreciated that the disease states and conditions mentioned hereinabove are the result of complex biological/biochemical phenomena and their etiology is not yet fully established. For example, vascular diseases are usually characterized by deposits of cholesterol within the blood vessels. Moreover, frank calcification of the vessels can sometimes, but not always, be noted. Tissue calcification sometimes occurs after tissue necrosis. "Diseases" such as senility and the like can be the result of a variety of processes involving degeneration of tissue, but it is generally accepted that some diminution of blood flow to the brain (with attendant hypoxia, ischemia and ultimate necrosis) is involved.

As noted hereinabove, the present treatment regimen involving phosphonates causes an increased rate of release of $O_2$ from the blood. The resulting increased efficiency of oxygen exchange at the tissue level would appear to be important means for combating any diminution or lack of tissue oxygenation, whatever the cause. However, it will be appreciated that the treatment of any bodily function, particularly disease states, most likely involves various unknown biological mechanisms. (For example, the mode of action at the molecular level of even an old drug such as aspirin has never been fully determined.) Accordingly, while the phosphonates herein appear to affect the blood/tissue oxygen interchange in a desirable manner, more subtle meechanisms which better account for their biological activity in the treatment of hypoxias and ischemias may be operating. In any event, the phosphonate compounds herein are useful for their intended purpose.

The organophosphonate compounds (or, more succinctly, "phosphonates") employed in the manner of this invention to treat, for example, cardiovascular diseases, various other diseases of the human vasculature system, including senility resulting from diminution of blood flow or decreased vascular network to brain centers, and like disease states, are of the type disclosed hereinafter.

The compounds which can be employed in the present invention are characterized by the phosphonate moiety ($-PO_3M_2$, wherein M represents H or a pharmaceutically acceptable cation or ester group). The phosphonates herein are organophosphonate, i.e., the phosphonate moiety is attached to a carbon atom by a carbon-phosphorus bond (C-P bond). The carbon atom, in turn, is bonded to other hydrocarbyl groups, e.g., alkyl phosphonates, or to hydrogen atoms, e.g., methane phosphonates, or to mixed hyrocarbyl groups, hydrogen atoms or other substituents, e.g., haloalkyl phosphonates. The hydrocarbyl groups can be substituted or non-substituted alkyl (including cycloalkyl), aryl (including heteroaryl) and the like. Substituent groups on the alkyl or aryl hydrocarbyl moiety can be, for example, additional phosphonate moieties; halogens, especially chlorine; carboxyl; esterified carboxyl; hydroxyl;

amino; amido; and the like. Preferred for use herein are organophosphonates having more than one C—$PO_3M_2$ group; diphosphonates, especially geminal diphosphonates characterized by the grouping

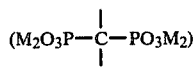

are most highly preferred.

The phosphonate compounds herein are administered at dosage levels judged to be "safe and effective" for their intended purpose. By an "effective" level is meant an amount sufficient to cause the desired physiological effect in the treatment regimen being used. By a "safe" level is meant that the risk:benefit ratio attendant with the administration of any drug composition is judged to be acceptable, according to the precepts of sound medical practice. Typical dosage levels are disclosed in more detail hereinafter, but these can be modified by the physician according to the needs of individual patients.

Typical phosphonate compounds useful herein are of the formula

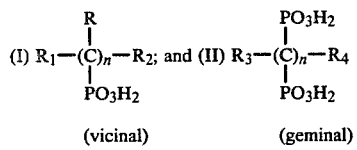

wherein n is an integer from 1 to about 10 and the substituent groups are H, alkyl, aryl, alkenyl, and the like. Examples of type I phosphonates are those wherein R, $R_1$ and $R_2$ are each hydrogen, alkyl, —$CH_2OH$ or are as noted for groups $R_3$ and $R_4$. Examples of type II phosphonates are those wherein $R_3$ is hydrogen, alkyl containing from 1 to about 20 carbon atoms, alkenyl containing from 2 to about 20 carbon atoms, aryl (e.g., phenyl and naphthyl), phenylethenyl, benzyl, halogen (e.g., chloriine, bromine, and fluorine), amino, substituted amino (e.g., dimethylamino, diethylamino, N-hydroxy-N-ethylamino, acetylamino), —$CH_2COOH$, —$CH_2PO_3H_2$, —$CH(PO_3H_2)(OH)$ or —$CH_2CH(PO_3H_2)_2$; $R_4$ is hydrogen, lower alkyl (e.g., methyl, ethyl, propyl, and butyl), amino, benzyl, halogen (e.g., chlorine, bromine and fluorine), hydroxyl, —$CH_2COOH$, —$CH_2PO_3H_2$, or —$CH_2CH_2PO_3H_2$, or a pharmaceutically acceptable salt thereof such as alkali metal (e.g., sodium and potassium), alkaline earth metal (e.g., calcium and magnesium), nontoxic heavy metal (e.g., stannous and indium), and ammonium or low molecular weight substituted ammonium (e.g., mono-, di-, and tri-ethanolammonium) salts. It will be appreciated that groups R, $R_1$ and $R_2$ and groups $R_3$ and $R_4$ can be cycloalkyl, heterocyclic or can be joined in ring structures, said rings being carbocyclic or heterocyclic.

The above described organophosphonic acids and their pharmaceutically-acceptable salts and esters are commonly referred to collectively as "phosphonates", "diphosphonates" or "polyphosphonates".

Operable phosphonates of the above formula (I) include propane-1,2,3-triphosphonic acid; butane-1,2,3,4-tetraphosphonic acid; hexane-1,2,3,4,5,6-hexaphosphonic acid; hexane-1-hydroxy-2,3,4,5,6-pentaphosphonic acid; hexane-1,6-dihydroxy-2,3,4,5-tetraphosphonic acid; pentane-1,2,3,4,5-pentaphosphonic acid; heptane-1,2,3,4,5,6,7-heptaphosphonic acid; octane-1,2,33,4,5,6,7,8-octaphosphonic acid; nonane-1,2,3,4,5,6,7,8,9-nonaphosphonic acid; decane-1,2,3,4,5,6,7,8,9,10-decaphosphonic acid; and the pharmaceutically acceptable salts of these acids, e.g., sodium, potassium, calcium, magnesium, ammonium, triethanolammonium, diethanolammonium, and monoethanolammonium salts.

Among the operable phosphonates encompassed by the above formula (II) are ethane-1-hydroxy-1,1-diphosphonic acid; methanediphosphonic acid; methanehydroxydiphosphonic acid; ethane-1,1,2-triphosphonic acid; propane-1,1,3,3-tetraphosphonic acid; ethane-2-phenyl-1,1-diphosphonic acid; ethane-2-naphthyl-1,1-diphosphonic acid; methanephenyldiphosphonic acid; ethane-1-amino-1,1-diphosphonic acid; methanedichlorodiphosphonic acid (dichloromethylene diphosphonic acid); nonane-5,5-diphosphonic acid; n-pentane-1,1-diphosphonic acid; methanedifluorodiphosphonic acid; methanedibromodiphosphonic acid; propane-2,2-diphosphonic acid; ethane-2-carboxy-1,1-diphosphonic acid; propane-1-hydroxy-1,1,3-triphosphonic acid; ethane-2-hydroxy-1,1,2-triphosphonic acid; ethane-1-hydroxy-1,1,2-triphosphonic acid; propane-1,3-diphenyl-2,2-diphosphonic acid; nonane-1,1-diphosphonic acid; hexadecane-1,1-diphosphonic acid; pent-4-ene-1-hydroxy-1,1-diphosphonic acid; octadec-9-ene-1-hydroxy-1,1-diphosphonic acid; 3-phenyl-1,1-diphosphonoprop-2-ene; octane-1,1-diphosphonic acid; dodecane-1,1-diphosphonic acid; phenylaminomethanediphosphonic acid; naphthylaminomethanediphosphonic acid; N,N-dimethylaminomethanediphosphonic acid; N-(2-hydroxyethyl)-aminomethanediphosphonic acid; N-acetylaminomethanediphosphonic acid; aminomethanediphosphonic acid; and the pharmaceutically acceptable salts of these acids, e.g., sodium, potassium, calcium, magnesium, stannous, indium, ammonium, triethanolammonium, diethanolammonium, and monoethanolammonium salts.

Mixtures of any of the foregoing phosphonic acids and/or salts can be used in the practice of this invention.

The geminal diphosphonates of formula (II) are most preferred for use herein.

Ethane-1-hydroxy-1,1-diphosphonic acid, an especially preferred geminal phosphonate, has the molecular formula $CH_3C(OH)(PO_3H_2)_2$ (according to nomenclature by radicals, the acid might also be named 1-hydroxyethylidene diphosphonic acid). The most readily crystallizable salt of this acid is obtained when two or three of the acid hydrogens are replaced by sodium. Preferred salts for the purpose of this invention are the trisodium hydrogen salt which has the structure:

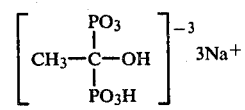

and the disodium dihydrogen salt.

The trisodium hydrogen salt normally crystallizes as the hexahydrate which loses some water during air-drying to yield a mixture of the hexa- and monohydrate averaging 3 to 4 molecules of water of hydration.

While any pharmaceutically acceptable salt of ethane-1-hydroxy-1,1-diphosphonic acid can be used in the practice of this invention, the tetrasodium salt, the trisodium hydrogen salt, the disodium dihydrogen salt, the monosodium trihydrogen salt, and the mixtures thereof are preferred. The other sodium, potassium, ammonium, and mono-, di-, and tri-ethanolammonium salts and mixtures thereof are also suitable, provided caution is observed in regulating the total intake of cation species in the salt composition. These compounds can be prepared by any suitable method; however, an especially preferred method is disclosed in U.S. Pat. No. 3,400,149, Sept. 3, 1968, incorporated herein by reference.

Methanehydroxydiphosphonic acid and related compounds operable herein can be prepared, for example, by the reaction of phosgene with an alkali metal dialkylphosphite. A complete description of these compounds and the method for preparing same is found in U.S. Pat. No. 3,422,137, O. T. Quimby, incorporated herein by reference.

Methanediphosphonic acid and related compounds useful herein are described in detail in U.S. Pat. No. 3,213,030, granted Oct. 19, 1965; a preferred method of preparing such compounds is disclosed in U.S. Pat. No. 3,251,907, granted May 17, 1966, incorporated herein by reference.

Ethane-1,1,2-triphosphonic acid and related compounds which can be used in this invention, as well as a method for their preparation, are fully described in U.S. Pat. No. 3,551,339, O. T. Quimby, incorporated herein by reference.

Propane-1,1,3,3-tetraphosphonic acid and related compounds useful herein, and a method for preparing same are fully disclosed in U.S. Pat. No. 3,400,176, O. T. Quimby, incorporated herein by reference.

Pentane-2,2-diphosphonic acid and related compounds can be prepared in accordance with the method described by G. M. Kosolopoff in *J. Amer. Chem. Soc.* 75, 1500 (1953), incorporated herein by reference.

Propane-1,2,3-triphosphonic acid and salts thereof can be prepared by a process disclosed in the application of D. Allan Nicholson and Darrel Campbell, Ser. No. 694,002, filed Dec. 27, 1967, now abandoned.

Butane-1,2,3,4-tetraphosphonic acid and salts thereof can be prepared by a process disclosed in the application of D. Allan Nicholson and Darrel Campbell, Ser. No. 694,003, filed Dec. 27, 1967, now abandoned.

The higher aliphatic vicinal polyphosphonates and salts thereof can be prepared by the process disclosed in U.S. Pat. No. 3,584,035, Nicholson and Campbell, incorporated herein by reference.

Substituted ethane diphosphonic acids and salts and esters thereof are disclosed in U.S. Pat. No. 3,940,436, issued Feb. 24, 1976, to A. F. Kerst, the disclosures of which are incorporated herein by reference. U.S. Pat. No. 3,944,599, to the same inventor, discloses geminal diphosphonate compounds having halogen and hydroxyl substituent groups, and the means for preparing same. The disclosures of this patent are also incorporated herein by reference.

Phosphonobutane tri- and tetra-carboxylic acid compounds and their preparation are disclosed in U.S. Pat. Nos. 3,886,204 and 3,886,205, both issued May 27, 1975, to Geffers, et al., the disclosures of which are incorporated herein by reference.

German 2360-798, June 26, 1975, to Henkel & Cie GmbH discloses pharmaceutical and cosmetic preparations for influencing the deposition of poorly soluble calcium salts, said preparations comprising polymethylene phosphonic acid compounds. This publication, the disclosures of which are incorporated herein by reference, describes the preparation of the phosphonate materials in detail.

The preparation and pharmacological properties of various amino phosphonate compounds are described in German 2343-146 (Mar. 6, 1975); Belgian 822-930 (June 4, 1975); Belgian 822-929 (Dec. 6, 1973); German 2360-711 (June 12, 1975); German 2360-719(June 6, 1975); Belgian 819-187 (Feb. 26, 1975); Belgian 819-188 (Feb. 26, 1975); and Belgian 819-189 (Feb. 26, 1975), the disclosures of said publications being incorporated herein by reference.

As can be seen from the foregoing, the preparation of the phosphonates used in the practice of this invention can be accomplished using well-known methods, or by simple modifications of various art-disclosed procedures. Only those organophosphonates which are pharmaceutically-acceptable (i.e., provide a satisfactory risk/benefit ratio) are contemplated for use herein. The well-known toxicity of some type (I) monophosphonates ($n=1$) disclosed in the structural formulas above precludes their use herein. However, such materials are known in the art and are easily avoided in the practice of this invention.

ANIMAL STUDIES (I)

Introduction

In the following ANIMAL STUDIES, typical phosphonate compounds of the type described hereinbefore were used. The studies involved ligation of the left anterior descending coronary artery to produce infarcts in the apical region of animal hearts. Of course, ligation causes a stoppage or drastic diminution of blood flow to a part of the heart organ. Properly done, temporary ligations of this type are occasioned by high survival rates in the test animals so that further studies can be concluded.

It will be appreciated that ligating the coronary artery in the manner disclosed hereinafter mimics, to the extent possible, arterial or vascular constructions or occlusions which can occur in various disease states and which result in hypoxia, ischemia and infarction of the involved organ. The heart organ is an excellent organ for research purposes, inasmuch as it is sufficiently large to allow detailed examination. In point of fact, the ligation technique substantially mimics what happens in the human body during myocardial infarction. However, the animal studies hereinafter are not meant to limit in any way the indications for use of the phosphonates to treat other types of hypoxias and tissue ischemias and infarcts involving other organs. In short, ligation of the coronary artery in the manner disclosed hereinafter was done for expediency to demonstrate the effectiveness of the phosphonate compounds for their intended purpose, and the results of this study can be extrapolated to other organs of the body.

Diphosphonates

Disodium ethane-1-hydroxy-1,1-diphosphonate (EHDP) and disodium dichloromethylene diphosphonate ($Cl_2MDP$) were obtained and their structures were confirmed by nuclear magnetic resonance and x-ray diffraction. Solutions (2.5%) of each compound were prepared by dissolving the stock powders in normal saline and adjusting the pH to 7.4 with NaOH.

Experimental Design

Ligation of the left anterior descending coronary artery was used in this study to produce infarcts in the apical region of the heart. This technique was chosen because of the high survival rate following temporary ligation of this vessel. In the first phase of the study, three untreated dogs were infarcted for the purpose of establishing the experimental procedure and the reproducibility of technique. Fifteen dogs were then randomly allocated to one of three treatment groups: saline (control), EHDP or $Cl_2MDP$. The diphosphonate-treated dogs received daily subcutaneous injections of 10 mg/kg body weight, while the control dogs received a comparable volume of saline. In all three experimental groups, the daily treatments were given for 7 days prior to surgery and continued for 5 days after infarction. On the day of the infarction, the treatment was administered approximately 2 hours prior to surgery. All animals were sacrificed on the morning of the 6th day post-infarction for gross and histopathological evaluation.

Experimental Methods

Healthy, purebred beagle dogs weighing approximately 10 kg were used in this study. Dogs were pre-anesthetized with injections of oxymorphone HCL (Numorphan, Endo Laboratories, Garden City, N.Y.), acepromazine (Ayerst Laboratories, New York, N.Y.) and atropine sulfate (Atrophine, W. A. Butler Co., Columbus, Ohio) and then started on an intravenous drip consisting of: electrolytes in 5% dextrose (Multisol, Abbott Laboratories, N. Chicago, Ill.), 2% lidocaine (Xylocaine, Astra Pharmaceuticals, Worcester, Mass.), penicillin (Pfizerpen, Pfizer Laboratories, New York, N.Y.), and sodium bicarbonate. The dogs were anesthetized with 2.5% sodium thiamylal (Surital, Parke-Davis, Detroit, Mich.), and anesthesia was maintained with methoxyflurane (Metofane, Pitman-Moore, Washington Crossing, N.Y.). A left thoracotomy was performed by an incision at the left fifth intercostal space. Once the thorax was entered, the Metofane vaporizer was closed and the dog placed on positive pressure resuscitation by means of a Bird Mark 2 ventilator. The left anterior descending coronary artery (LADC) was exposed at the ventral interventricular groove of the heart and dissected from the adjacent tissue. The artery was ligated at a site mid-distant between the first two vessels branching posteriorly from the LADC using 00 silk ligature tied over a piece of silastic tubing. The vessel was completely occluded for a period of 2 hours, after which the ligature was released and the chest closed by standard thoracotomy closure. Following surgery the dogs were placed in an oxygen cage for the next 6-8 hours before being returned to their regular cages. Body temperatures were monitored daily for 4 days post operatively and daily injections of penicillin (Procaine Penicillin G, 600,000 units) were given for 3 days following surgery.

Electrocardiograms (ECG's) were taken at three different times prior to surgery (including the morning of surgery), immediately following surgery, and at 6, 24, 48 and 72 hours post-infarction. Leads I, II, III, AVR, AVL, AVF and $V_{10}$ were used in all electrocardiographic examinations. A lead II ECG and heart rate were continually monitored throughout surgery.

Blood samples were taken from each dog prior to surgery (baseline), at 3 times during surgery, and at 6, 8, 10, 12, 24, 48 and 72 hours post infarction. All sera were prepared immediately after collection and stored at 2° C. until analyzed. The following enzymes were measured in each serum sample: creatine phosphokinase (CPK), by the method of Rosalki; lactic dehydrogenase (LDH), by the method of Wacker, et al.; glutamic oxalacetic transaminase (SGOT), by the method of Henry, et al.; and alpha-hydroxybutyric dehydrogenase ($\alpha$HBD), by the method of Rosalki and Wilkinson.

Estimation of Gross Infarct Size

On the morning of the 6th day post-infarction, the dogs were anesthetized with Surital and 4 dogs from each group were killed by perfusion fixation of their hearts using 10% aqueous formalin buffered with phosphate to pH 7.0. The hearts were immediately excised and stored in the fixative. For estimation of gross infarct size, the hearts were sliced into approximately 0.2-0.3 cm sections. The infarct was identified grossly either by its pale appearance compared to unaffected myocardium or by the presence of hemorrhage in the infarcted tissue. The size of the infarct tissue was estimated by superimposing on each slice of clear plastic overlay containing an arrangement of random dots. The relative areas occupied by normal and infarcted tissue were assessed by counting the number of dots which fell on each type of tissue. The estimated areas were then summed from all the slices and the gross infarct size calculated as a percent relative to the total myocardial area.

Histopathology

Five separate sections of myocardium were collected from each dog for histopathological evaluation. Section 1 was taken from a non-involved area of the heart, sections 2 and 3 from the peripheral zone of the infarcted area, and sections 4 and 5 from the center of the infarct.

Sections 0.2-0.3 cm in thickness were embedded in paraffin and serial 5-8 micron thick sections stained with hematoxylin and eosin (H&E), Gomori aldehyde fuchsin trichrome (Gaft), and Alazarin Red S. Tissue sections were examined by an independent observer without knowledge of the treatment given each animal. For comparative purposes, the lesions were graded according to the following scale: grade 0=no lesion; grade 1=less than 25% of the cross-sectional area involved, i.e., degenerated and necrotic; grade 2=25-50% of the area involved, grade 3=50-75% of the area involved; grade 4=75-90% of the area involved.

Electron Microscopy

For electron microscopic examination, a technique was used for the histochemical localization of calcium. The histochemical stain employed was potassium pyroantimonate which forms an electron dense precipitate with divalent cations such as calcium. The following method was used in the study. Three dogs (1 from each treatment) were anesthetized with Surital and killed by perfusion fixation of their hearts with a solution of 0.5% glutaraldehyde saturated with potassium pyroantimonate. The hearts were excised and immediately placed in a solution of 2% gluaraldehyde saturated with potassium pyroantimonate. After fixation, the hearts were sliced into 0.2-0.3 cm thick sections to disclose the infarcted area. Thin sections were then taken from the center of each infarct and processed for electron microscopy.

Statistical Analysis

The serum enzyme values were subjected to statistical evaluation using Dunnett's procedure for comparison of group mean values versus control, and also using a distribution-free analog of Dunnett's test.

Results

Analysis of the electrocardiograms, which was conducted by an independent observer without knowledge of the treatment given each animal, revealed differences among the saline and drug treatment groups. Dogs treated with saline and $Cl_2MDP$ had more severe arrhythmias persisting throughout the 72-hour examination period as compared with the dogs treated with EHDP. Two of the four dogs treated with EHDP demonstrated severe cardiac arrhythmias within 24 hours post infarction, but returned to normal or showed only occasional premature ventricular contraction by 72 hours. The other two dogs treated with EHDP did not domonstrate any ectopic rhythm. Dogs treated with $Cl_2MDP$ showed electrocardiographic changes similar to the control group in the earlier stages following infarction. Arrhythmias developed in 6 hours and became quite severe by 24 hours. By 72 hours, all but one dog treated with $Cl_2MDP$ either had returned to normal or showed only an occasional premature ventricular contraction. On the other hand, two of four dogs treated with saline experienced severe cardiac arrhythmias throughout the 72 hour examination period. The numbers were not great enough for statistical comparison of groups, but the data indicate the following order of severity of arrhythmias among the test groups: saline control $> Cl_2MDP >$ EHDP.

Results of serum enzyme analyses demonstrated that there were no statistically significant differences ($p<0.05$) between treatment groups when the group mean values at the baseline, 6, 12, 24, 48 or 72-hour periods were compared, or when values calculated as percent change from baseline were compared. Because of the extremely large elevations and the considerable variability of baseline values among the test groups, the data were also examined by a distribution-free (rank sum) statistical test. Again, differences in rank sum averages between the test groups were not statistically significant ($p<0.05$), although there appeared to be a trend toward lower enzyme elevations in the EHDP and $Cl_2MDP$ groups, compared with control. An additional complicating factor was the occurrence of hemolysis in many of the blood samples. Hemolysis did not appear to be treatment-related, but occurred in the majority of samples collected between 6 and 12 hours post infarction. Hemolysis was not a problem in those samples collected either prior to the 6-hour post-infarction period or those collected beyond 12 hours following infarction. The reason for this phenomenon was not determined, but undoubtedly was related to the experimental procedure. Because of the interference of hemolysis on the serum levels of LDH and $\alpha$HBD, the latter enzyme values were considered inappropriate as indicators of myocardial ischemic injury in this study. On the other hand, hemolysis has negligble or only minimal effects on the serum levels of SGOT and CPK, and therefore, these values were considered meaningful as indicators of ischemic injury.

Estimates of gross infarct size by planimetry demonstrated that in the saline-treated dogs gross infarct size was consistently small and was observed to range between 5.3% and 7.4%. In the EHDP treatment group, two of the four dogs displayed infarct sizes of 6.8% and 8.1%, which are in the same range as the saline controls. The other two EHDP-treated dogs, however, had infarcts which were estimated to be 2.4% and 0.2%. Similar variability was observed in the $Cl_2MDP$ group, where one dog displayed an infarct estimated at 7.8%, while the other two dogs had infarcts of 1.5% and 0.9%. Because of the small number of animals in the treatment groups and the high variability, statistics were not applied to these data.

Histopathology

The major lesions observed upon histopathologic examination of the myocardium of dogs in this study consisted of degeneration and necrosis of the myocardial cells. The endocardial one third of the wall was most severely affected, the mid-wall one third was less affected, and the epicardial one third was the least affected.

The lesions consisted of myofiber degeneration and necrosis, with loss of striations, eosinophilic staining of cells at the periphery of nodular or focal lesions, loss of nuclei, contraction bands, and finally, in the most severe areas, complete loss of the myofibers and replacement with fibrous connective tissue. The areas of necrosis varied from individual cells or small clusters of cells, through small scattered patches of necrosis 1-3 mm diameter, up to large confluent masses of necrosis which occupied the entire section. The necrotic areas were always surrounded by cardiac histiocytes at the junction of the necrotic tissue with the viable tissue, and there was moderate variable fibroblastic infiltration, depending on the severity of necrosis. In some areas, cells were better preserved than in other areas, and gave the suggestion that some cells may have been only moderately damaged.

Capillaries were generally closed, or contained small numbers of erythrocytes in the necrotic areas, but the larger arterioles and arteries were generally widely patent. Thrombi generally were not present, but were found in an epicardial coronary artery in one dog, and in a smaller intramural coronary artery in a second dog. Hemorrhage into the larger necrotic zones was common but not extensive.

In one dog there were basophilic droplets ranging in size from 1–10$\mu$ aligned in streaks in the interstitial areas in the necrotic zones. These droplets stained red with the trichrome stain, negative for calcium, and probably represented protein droplets in the tissue from cellular breakdown.

Intracellular calcium was found in only one dog, and was present as fine droplets as basophilic material which were Alizarin Red positive.

No areas of necrosis were identified histologically in areas of myocardium selected as normal tissue based upon gross observation of the tissue.

In sections of tissue selected from the peripheral region of the infarct, the trend was for both EHDP and $Cl_2MDP$ to have some protective effect in the midportion of the myocardium.

Evaluation of sections from the center of the infarct demonstrated a trend in all groups with the least amount of necrosis in the epicardial third of the wall and most widespread necrosis in the endocardial one third of the wall. However, the amount of necrosis in the epicardial regions was reduced by both diphosphonate treatments. (Neither drug had an obvious protective effect on either the midportion or endocardial region.)

Ultrastructural evaluation of tissue from the infarcted myocardium from a saline-treated dog demonstrated that the orderly pattern of myocardial fibers was no longer demonstrable, mitochondria were vacuolated and Z bands, M bands and A and I zones were not readily recognizable. There was diffuse distribution of pyroantimonate granules (a calcium stain) throughout the tissue with no suggestion of a distribution of stain along any membrane or on any cytoplasmic structure.

In infarcted myocardium from the EHDP-treated dog, occasional mitochondria appeared dilated but most had distinct intact outer membranes and cristae. Z bands, M bands and A and I zones of the sarcomere were readily demonstrated. Pyroantimonate was concentrated along the sarcolemma and within the sarcoplasmic reticulum between adjacent muscle fibers. In none of the electron photomicrographs evaluated from this dog was there evidence of diffuse scattering of electron dense pyroantimonate granules as seen in the tissue from the saline-treated dogs.

In myocardium from a $Cl_2MDP$-treated dog the orderly pattern of cross striations representing Z bands was consistently present. The electron dense pyroantimonate stain was concentrated along sarcolemmal membranes, around the periphery of vessels and in the sarcoplasmic reticulum. However, a consistent finding in the myocardial cells of this animal was a pronounced swelling of the mitochondria with loss of much of the ultrastructurally demonstrable internal cristae. Cristae were still demonstrable around the polar region of each mitochondrion.

ANIMAL STUDIES (II)

Introduction

Both direct and indirect techniques have been employed to assess various potential therapeutic approaches to the protection of ischemic myocardium. Epicardial or precordial electrocardiographic leads or serial serum creatinine phosphokinase (CPK) determinations are indirect indices that have been used extensively to assess the extent of myocardial damage and various modes of protection. The biochemical or physical determinants of these indices are not necessarily determinants of myocardial cell damage. Therefore, the correlation between these indices and irreversible myocardial injury may not always be precise. Nevertheless, these indirect techniques, which have been used in a number of studies, are the only means currently available for assessing therapy in man.

In the present studies, a more direct approach is used to evaluate the effect of drug therapy on infarct size. The temporary occlusion model used in this study was developed to enable anatomic quantitation of ischemic cell death in order to evaluate therapies which could potentially reduce infarct size. This model uses a relatively brief (40 minutes) period of coronary occlusion and only severely ischemic myocardium dies even in untreated dogs. Thus the model is useful for evaluating drug effect on severely ischemic myocardium but, by definition, does not provide a test of drug effect on mildly ischemic cells around the periphery of a developing infarct which might undergo necrosis following a more prolonged period of coronary occlusion and/or a more prolonged period of repair following occlusion than the 48 hours chosen, i.e., chronic effects of occlusion as opposed to acute. Thus, this model does not entirely reproduce the process of myocardial infarction as it occurs in man. On the other hand, it is reasonable to hypothesize that the mechanism of cell death is similar in severely and mildly ischemic areas even though irreversible injury occurs over a much slower time scale in areas of mild ischemia.

The temporary occlusion model has several advantages. Hemodynamic parameters can be continuously monitored and the brief period of occlusion minimizes fluctuation of these parameters during the ischemic period. Quantitation of necrosis is done within transmural sections through the posterior papillary (PP) muscle. Analysis in this manner provides an index of the overall infarct size and minimizes variation in lateral extent of the infarct which is strongly influenced by dog-to-dog variation in coronary anatomy. The 48-hour period of reperfusion is optimal because it allows areas of cells which were irreversibly injured during coronary occlusion to develop characteristic features of necrosis, but is early enough to avoid reduction of necrotic areas by significant phagocytic removal of dead cells.

The amount of necrosis in untreated dogs varies considerably in this model and in the present study varied from 13% to 92% of the anatomic PP. The total experience with about 60 untreated animals indicates a normal distribution with a mean of approximately 60% necrosis of the anatomic PP. The dogs in the present study thus are representative of the total population. Because of the dog-to-dog variation, detection of positive effects with a therapeutic intervention requires the use of relatively large groups of dogs. With a test population size of 8–10 dogs, reduction of necrosis by 30% or more usually becomes detectable by standard statistical methods.

SUMMARY OF RESULTS

To summarize the results of the present study, several dogs in the EHDP treated group had rather large areas of necrosis. On the other hand, small amounts of necrosis are occasionally observed in untreated dogs and this also occurred in the present study. Thus, it is not possible to be certain whether EHDP was effective in any particular dog. The overall reduction of necrosis by EHDP was 30%–40%. Because of the considerable variability observed, this apparent reduction in necrosis observed with EHDP was not statistically significant when only the dogs in this study were considered. The effect observed does become significant when larger numbers of dogs are obtained by including untreated dogs from a concurrent study with the drug Verapamil as part of the control group in the EHDP study. Thus, it seems likely that the protective effect of EHDP is small and is less than the effects observed in similar studies with Propranolol, mannitol or Verapamil. On the other hand, the protective effects observed with both Propranolol and Verapamil in other studies were associated with hemodynamic side effects (depressed cardiac function) which may be undesirable in some patients. The reduction of necrosis with EHDP, while less impressive, occurred without hemodynamic or chemical side effects. Thus, in comparison with the other drugs tested, EHDP seems less likely to have major contraindications to use, either alone or as part of a combination drug regimen.

Experimental Methods

Mongrel dogs of either sex weighing 20–29 lbs. in apparent good health and free of heart worm filaria were anesthetized with sodium pentobarbitol (approximately 30 mg/kg i.v.) and ventilated with a Harvard 1063 respirator. Six hundred thousand units of bicillin was given I.M. prophylactically prior to the surgical procedure. Lead II of the standard ECG was monitored continuously on a Brush Model 440 recorder. Sterile instruments, sponges and drapes were used during the surgical procedure. Catheters were placed in the femoral artery and vein via the saphenous branches to monitor peripheral blood pressure and for fluid and drug administration respectively. Blood was drawn for hematocrit, sedimentation rate, and SMA-12 (includes serum calcium and phosphorus) prior to thoracotomy. All dogs were given 100 cc of normal saline via i.v. infusion for blood and fluid replacement during the acute experiment.

The chest was opened through the left 4th or 5th interspace and the pericardium was opened. A catheter was placed in the left ventricle via the left atrial appendage to monitor ventricular pressures. The circumflex artery was isolated 1–2 cm from the aorta.

Coronary occlusions were done in two randomized groups of dogs:

EHDP Treated Dogs were given 5.0 mg/kg EHDP i.v. in 5–10 cc of normal saline 10 minutes prior to coronary occlusion.

Control Dogs were given 5–10 cc of normal saline without drug 10 minutes prior to occlusion.

The circumflex artery was occluded for 40 minutes by a silk snare to produce postero-lateral left ventricular ischemia. Hemodynamic parameters including heart rate, systolic, mean, and diastolic blood pressure, ventricular systolic and end diastolic pressure and LV peak dP/dt were recorded on a Brush Model 440 Recorder before and after drug infusion (prior to occlusion) and at 5, 20 and 38 minutes after occlusion. A second SMA-12 was obtained 20 min. post-occlusion. EHDP treated dogs were given an additional 5.0 mg/kg of EHDP subcutaneously at the end of the acute experiment and B.I.D. beginning the evening of the day of occlusion.

After 40 minutes of ischemia, reflow was instituted by removal of the snare, incisions were closed, and dogs were allowed to recover for 48 hours. Dogs were then reanesthetized and the chest reopened. The heart was then excised and weighed. The exact location of occlusion and any evidence of coronary injury or thrombosis was noted.

The endocardial surface of the left ventricle was photographed. Transmural slices through the posterior and anterior papillary muscles were cut, photographed, and fixed in formalin. Histologic sections were cut and stained with Hematoxylin and Eosin, PAS for glycogen, and Heidenhain's variant of Mallory's connective tissue stain. Necrosis in the posterior papillary muscle was quantitated from tracings of the projected images of the histologic sections.

Results

Proximal occlusion for 40 minutes of the circumflex branch of the left coronary artery followed by 48 hours of reperfusion characteristically results in necrosis involving the subendocardial myocardium of the postero-lateral wall of the left ventricle. The injury is usually greatest within the posterior papillary muscle. Histologically, necrosis following such temporary ischemia is well defined on H&E sections and is characterized by myocardial fibers which have a homogeneous glassy cytoplasm with partial loss of cross striations, or with contraction bands. There is either nuclear pyknosis or karyolysis. There is an intense inflammatory reaction which is often particularly prominent on the periphery of the necrotic areas. Necrotic areas, when stained with Heidenhain's variant of Mallory's connective tissue stain, show prominent contraction bands which give cells in the necrotic areas a granular appearance easily seen at low power. Projection of such slides onto photographic paper allows quantitation of necrotic areas within a given section of heart muscle.

Untreated Controls

In 9 untreated dogs which survived without developing ventricular fibrillation following 40 minutes of occlusion and 48 hours of reperfusion, $36\pm7\%$ of muscle in transmural sections through the posterior papillary muscle was necrotic. Most of this injury occurred in the posterior papillary muscle, per se, where $58\pm9\%$ of fibers were necrotic. Two additional dogs which developed ventricular fibrillation at the time of reperfusion but were successfully resuscitated, showed greater than average amounts of necrosis and when these two dogs were included the overall amount of necrosis was $38\pm6\%$ and $59\pm8\%$ of the transmural papillary muscle and anatomic PP, respectively.

Hemodynamic effects associated with coronary occlusion in the untreated group included a modest fall in left ventricular systolic pressure ($p<0.005$) and modest rise in LV end diastolic pressure ($p<0.01$). Changes in the other hemodynamic parameters measured at 20 minutes after occlusion were minimal. The two dogs resuscitated from VF had abnormally fast heart rates throughout the experiments.

Serum calcium did not change following thoracotomy and coronary occlusion. Serum phosphorus fell from 5.5 to 4.3 ($p<0.05$). Serum chemistries were not significantly altered from preocclusion values.

EHDP Treated Dogs

Ten dogs pre-treated with EHDP survived without developing ventricular fibrillation. After 40 minutes of circumflex occlusion and 48 hours of reperfusion, $22\pm5\%$ of the transmural sections through the PP was necrotic. This was not significantly different from necrosis in the untreated group. As in the untreated group, necrosis was most prominent in the PP per se. EHDP treated dogs showed $42\pm7\%$ necrosis of the anatomic PP. This also was not significantly different from the necrosis observed in the untreated dogs. Inclusion of one dog which developed reflow ventricular fibrillation but was successfully salvaged by countershock, did not alter the experimental results.

Treatment with EHDP, per se, had no hemodynamic effects during occlusion as opposed to the expected depressed cardiac function associated with drugs such as Verapamil and Propranolol. Similar to the untreated group, dogs given EHDP showed modest reductions in LV developed pressure ($p<0.05$) and mean blood pressure ($p<0.001$) 20 minutes after occlusion.

Dogs treated with EHDP had no change in serum calcium measured 20 minutes following coronary occlusion. As in the untreated dogs, serum phosphorus dropped slightly but consistently ($p<0.001$) during this time period. All other serum chemistries were unaltered by EHDP or coronary occlusion.

ST Segment Elevation

Standard limb lead 11 peak ST segment elevation was recorded as an additional index of ischemic injury. Dogs treated with EHDP showed less ST segment elevation compared with the untreated group.

Mortality

The incidence of ventricular fibrillation during the 40 minute occlusion was relatively low in this study (5 of 36 dogs of which 2 were untreated and 3 were EHDP treated). Ventricular fibrillation associated with reflow is a significant complication in this particular model and occurred in 9 dogs (6 untreated and 3 EHDP dogs). Of these, 3 were successfully defibrillated (2 untreated, 1 EHDP treated). Three dogs which survived occlusion and reperfusion died overnight and were excluded from morphologic analysis. Thus the overall survival in this study was identical (61%) in the two groups.

Discussion

Although not a high statistical probability (90% confidence in the decrease by EHDP of necrosis without additional controls; 97.5% confidence in decrease with additional controls), the decrease in damaged myocardium elicited by EHDP is surprising especially when the extended periods of low blood concentration between bolus injections over the 48 hour recovery period are considered (sc & iv bolus injections not continuous infusion to maintain constant blood level). This study, although of a probe nature, suggests that EHDP produces a protective effect on myocardium made ischemic by temporary ligation of the circumflex artery.

BLOOD STUDIES

Introduction

In the present study, resonance Raman spectroscopy was used to determine the effect of EHDP on the rate of deoxygenation of diluted, whole human blood, in vitro. Experiments with blood from dogs were not successful, since an unacceptably high level of rupturing of the dog blood cells occurred during experimental manipulation. (This is consistent with other observations that dog red blood cells are more fragile than human blood cells.)

Experimental Methods

Resonance Raman spectroscopy deals with the same basic inelastic light scattering effect that occurs in Raman spectroscopy (i.e., irradiation of a sample with monochromatic light and dispersing the resulting scattered light through a monochromator to detect the small amounts of radiation that are shifted in wave length from that of the incident light beam). Under conditions of resonance, the incident monochromatic light is at, or very close to, an electronic transition of the molecule being studied. When this resonance exists, there is a selective enhancement in the inelastically scattered light intensity associated with some of the molecular vibrations of the chromophore (that part of the molecule containing the electronic transition). This can occur for hemoglobin (Hb) and resonance Raman spectra of Hb provide detailed information on the vibrations of the heme (Fe-containing porphyrin ring) groups of the molecule at very low solution concentrations ($10^{-4}$–$10^{-7}$ M) where the Raman spectrum of the remaining portions of the Hb molecule are too weak to be observed. Since resonance Raman spectroscopy is a sensitive probe of the heme structure in Hb, it is used in the present experiment to measure oxy-Hb and deoxy-Hb in whole blood, and to measure the effects of phosphonates on the rate of deoxygenation (oxy-Hb to deoxy-Hb transition) of blood.

Raman spectra were recorded on a Spex Ramalog 5 laser Raman spectrometer equipped with a Coherent Radiation Model CR-3 $Ar^+$ laser. The 514.5 nm $Ar^+$ laser line (attenuated to $\lesssim 50$ m watts at the sample) was used for excitation of the resonance Raman spectra.

The Raman vibrational bands at 1640 $cm^{-1}$ (oxy-Hb) and 1607 $cm^{-1}$ (deoxy-Hb) were used as the oxygen "marker" vibrations. The intensity of the bands is approximately linearly proportional to the concentration of Hb species in dilute solution.

When testing pure Hb solutions ($\sim 10^{-5}$ M), samples were placed in a small cylindrical glass cell ($\sim 1.5$ ml volume), and deoxygenation of the Hb was effected by flushing an atmosphere of pure $N_2$ through the upper part of the cell above the solution (no stirring was used in these experiments). The Raman scattered intensities at 1640 and 1607 $cm^{-1}$ were recorded as a function of the time under $N_2$. Rates of deoxygenation of the Hb were measured from these data for pure Hb solutions and Hb solutions with added ($\sim 10^{-5}$ M) EHDP.

Diluted whole blood solutions ($\sim 1$–2 drops of whole blood—20 to 40 microliters per ml of pH 7 saline solution) could not be studied via the technique as described above for the pure Hb samples since the whole blood cells rapidly settled out of suspension long before deoxygenation occurred. To maintain a thoroughly agitated suspension, it was necessary to modify the system, as follows. Two mls of diluted whole blood solution were placed in a 10 ml Erlenmeyer flask that had been modified by the addition of a small capillary-size drain tube at the lowest point in the flask. Capillary size Tygon ® tubing was used to make a closed loop from the drain tube on the 10 ml reservoir flask back to the top of the flask. A short piece of glass capillary was inserted into the tubing loop and used as the Raman sampling cell. A peristaltic pump was used to flow the solution through the tubing at a rate of approximately 1.2 ml/min. Thus, the total diluted blood sample volume was cycled through the sample cell approximately every 100 seconds. The inner walls of the entire closed system were treated with Siliclad ®, a commercial siliconizing agent specifically developed to minimize the rupturing of blood cells. To verify that the red cells were not extensively ruptured, red blood cell counts were performed on three different blood samples. It was noted that $\lesssim 10\%$ of the blood cells were ruptured during the $\sim 1\frac{1}{2}$ hours of pumping required to complete one measurement. The number of ruptured red cells appeared to be independent (to ±1%) of the presence of EHDP in the blood sample.

Because of the slow deterioration of the blood sample during each experiment, it was necessary to start each deoxygenation measurement with a fresh blood sample. To assure a direct comparison of the effect of EHDP (or the other additives used) to each given blood sample, the blood solutions were divided into two (2 ml) portions. In half of the experiments, the first blood sample to be deoxygenated was treated with the EHDP and the second portion of the same blood sample was used as a control and deoxygenated with no additives present. In the remaining half of the experiments, the treated and control experiments were run in reverse order.

The concentration of blood used in the experiments was varied by a factor of two and no observable change in the overall time required for deoxygenation or in the accuracy of results was observed. The fact that there was no change in the total time required for deoxygenation of solutions with blood concentrations varying by a factor of two (with a constant surface and $N_2$ sweep rate) indicated that diffusion through the plasma, while important, cannot be the total rate controlling process, since if it were, doubling the $[O_2]$ that has to diffuse from the solution would be expected to increase the total time required for diffusion from the solution, thus making the total deoxygenation time somewhat longer.

SUMMARY OF RESULTS

Raman spectra from the present study demonstrated that the addition of EHDP to diluted whole blood solutions (ca. 100–200 μl of whole blood diluted in 5 ml saline with $10^{-5}$ M EHDP) causes a ca. 20% increase in the rate of deoxygenation of the blood. $Cl_2MDP$ effected an increase in rate for $O_2$ release but was less effective than EHDP in the same study.

As can be seen from the foregoing, the physiological response demonstrated in the in vitro BLOOD STUDIES correlates well with the therapeutic benefit shown in the in vivo ANIMAL STUDIES. While various unknown biological/biochemical processes may also be involved, the results of the studies comport with the simple overall "picture" of phosphonate drug action disclosed hereinabove, i.e., increasing the rate of release of $O_2$ from blood to tissues is beneficial in preventing tissue damage caused by oxygen starvation.

PREFERRED MODE

Within the scope of sound medical judgment, the dosage of phosphonates will vary with the particular condition being treated, the severity of the condition, the duration of treatment, and the specific phosphonate employed. However, single dosages can range from 0.01 to 500 mg. per kilogram of body weight, preferably 0.5 to 50 mg/kg (unless otherwise specified, the unit designated "mg/kg" as used herein refers to mg/kg of body weight). The higher dosages within this range are usually required in the case of oral administration because of limited absorption. Up to four dosages per day can be used routinely, but this can be varied to the needs of the patient, consistent with a sound benefit:risk ratio. Dosages greater than about 500 mg/kg may produce toxic symptoms and are usually avoided. Moreover, daily dosages greater than about 2,000 mg/kg are not ordinarily required to produce the desired benefit and may produce toxic side effects. Oral dosages of less than about 0.01 mg/kg do not materially affect $O_2$ release, but may be useful if administered intravenously.

Preferably, dosages ranging from about 10 to about 100 mg/kg are employed when the phosphonates are administered orally, since absorption is not total.

For parenteral administration (s.c., i.p., i.m.), dosages are preferably from about 0.5 mg/kg/day to about 20 mg/kg/day. For long-term parenteral infusion (i.v.) the most highly preferred dosage range is from about 5 mg/kg/day to about 10 mg/kg/day.

Table 1, below, sets forth typical dosages for various conditions which can be treated in accordance with this invention:

TABLE 1

| Condition | Oral dosage (mg/kg) Up to four times/day* |
|---|---|
| Retinopathy | 0.05–25 |
| Chronic Renal Failure | 0.05–25 |
| Myocardial Infarction | 0.05–50 |
| Senility | 0.05–25 |
| Pernicious Anemia | 0.05–25 |

*A larger initial dosage may be required, e.g., up to 500 mg/kg followed by the specified dosage level.

The phosphonates can also be administered parenterally in aqueous solution by subcutaneous, intradermal, intramuscular or intravenous injection, or i.v. infusion. The usual, and preferred, dosage ranges by these modes of administration are as follows:

| Subcutaneous | 0.05–10 mg/kg |
| Intradermal | 0.05–10 mg/kg |
| Intramuscular | 0.05–5 mg/kg |
| Intravenous | 0.05–5 mg/kg |

For direct inhalation therapy of chronic hypoxic lung disorders, aerosol sprays delivering 0.1–10 mg/kg/day of phosphonate can be used.

For purposes of oral administration the phosphonates can be formulated in the form of capsules, tablets or granules. For treatment of non-human animals, the phosphonates are preferably incorporated in animal feed, feed supplements or feed concentrates. They can also be prepared in unit dosage form together with a pharmaceutical carrier, each unit dosage form containing from ca. 15 mg to 10 g of phosphonate. The preferred concentration range of phosphonate in unit dosage forms intended for use by humans and smaller domesticated animals is from 15 mg to 1,000 mg, more preferably 100 mg to 500 mg. A higher concentration range, i.e., from 1 g to 5 g is preferred in unit dosage forms intended for treatment of larger animals such as cattle, horses, etc.

When administered orally, the compositions used in this invention are preferably in a form adapted to minimal exposure of the phosphonates to the oral cavity. Although these compounds do not damage dental enamel when applied to the tooth surfaces at the relatively low concentrations typical of toothpaste, mouthwash, lozenges and the like intended for dental calculus prophylaxis, the substantially higher concentrations of phosphonates provided in the unit dosage form embodiments of this invention may demineralize dental enamel on repeated prolonged exposure. Thus oral administration is preferably effected with such unit dosage forms as capsules, pills, and tablets which are promptly ingested. Troches, chewable tablets and the like which typically remain in the oral cavity for a substantial time prior to ingestion are preferably avoided.

As used herein, the term "pharmaceutical carrier" denotes a solid or liquid filler diluent or encapsulating substance. Some examples of the substances which can serve as pharmaceutical carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; pyrogen-free water; isotonic saline; and phosphate buffer solutions, as well as other non-toxic compatible substances used in pharmaceutical formulations. Wetting agents and lubricants such as sodium lauryl sulfate, as well as coloring agents, flavoring agents and preservatives, can also be present. Tableting is done using conventional techniques.

The pharmaceutical carrier employed in conjunction with the phosphonates is used at a concentration sufficient to provide a practical size to dosage relationship. Preferably, the pharmaceutical carrier comprises from about 0.1% to 99% by weight of the total composition.

Animal feed compositions to which the phosphonates of this invention can be added generally include as feedstuffs a cellulosic roughage component such as hay, straw, plant hulls, corn cobs, etc. Protein-containing components such as whole grains, including corn, wheat, barley, oats, rye, millet and alfalfa are typically included.

It will be appreciated that the present invention is useful not only in humans (see disease states disclosed hereinabove), but also in lower animals to treat similar disease states involving obstruction or stenosis of blood vessels to tissues or organs, or to alleviate tissue hypoxia caused by over-exertion or exposure to high altitudes.

The following examples illustrate compositions and methods used in the practice of this invention, but are not intended to be limiting thereof.

EXAMPLE I

Gelatin capsules are prepared by conventional methods, comprising as follows:

| Ingredient | Mg per Capsule |
|---|---|
| EHDP* | 350.00 |
| Starch | 50.00 |

*Mixture of di- and tri-sodium salts.

The above capsules administered twice daily substantially increase the rate of blood oxygen release in a 70 kg. human patient having need of such treatment.

Similar results to those obtained with the capsules of Example I are secured when the EHDP salts are replaced by an equivalent amount of EHDP (free acid form), and the following phosphonates, respectively: methanediphosphonic acid, methanedichlorodiphosphonic acid, methanehydroxydiphosphonic acid, ethane-1-amino-1,1-diphosphonic acid, phenylaminomethanediphosphonic acid, N,N-dimethylaminomethanediphosphonic acid, N-(2-hydroxyethyl)-aminomethanediphosphonic acid, N-acetylaminomethanediphosphonic acid, aminomethanediphosphonic acid, hexane-1,2,3,4,5,6-hexaphosphonic acid, and pent-4-ene-1-hydroxy-1,1-diphosphonic acid.

EXAMPLE II

Tablets are prepared by conventional methods, formulated as follows:

| Ingredient | Mg per Tablet |
|---|---|
| EHDP* | 25.00 |
| Lactose | 40.00 |
| Starch | 2.50 |
| Magnesium stearate | 1.00 |

*Mixture of di- and tri-sodium salts.

When administered orally four times daily, the above composition significantly reduces hypoxia and tissue damage associated with coronary insufficiency in a patient weighing approximately 70 kilograms, having a predisposition to myocardial infarction.

Similar results are achieved with tablets formulated as above but replacing EHDP with the disodium salt of ethane-1-hydroxy-1,1-diphosphonic acid, the trisodium salt of methanediphosphonic acid, the disodium salt of methanehydroxydiphosphonic acid, aminomethanediphosphonic acid, the monosodium salt of methanedichlorodiphosphonic acid, naphthylaminomethanediphosphonic acid, propane-1,2,3-triphosphonic acid, the pentasodium salt of butane-1,2,3,4-tetraphosphonic acid, the monoindium salt of octadec-9-ene-1-hydroxy-1,1-diphosphonic acid, the monostannous salt of hexadecane-1,1-diphosphonic acid, and propane-1,1-diphosphonic acid, respectively.

The lactose employed in this example is replaced by sucrose and the magnesium stearate by sodium carboxymethylcellulose without affecting the desired properties of the tablet.

EXAMPLE III

The phosphonate compositions of Example II are administered prophylactically four times daily to a 70 kg. patient suffering with diabetes mellitus, and predisposed to diabetic retinophathy, to preserve sight.

EXAMPLES IV–XVI

Solutions for parenteral administration are prepared by dissolving the following phosphonates in distilled water at the specified concentration, adjusting the pH to 7.4 with the base corresponding to the indicated salt form, or sodium hydroxide in the case of the acids, and sterilizing same by standard sterilization techniques.

| Ex. | Phosphonate | Conc. mg/ml |
|---|---|---|
| IV | Disodium salt of ethane-1-hydroxy-1,1-diphosphonic acid | 10.0 |
| V | Monopotassium salt of ethane-1-hydroxy-1,1-diphosphonic acid | 15.0 |
| VI | Diammonium salt of ethane-1-hydroxy-1,1-diphosphonic acid | 5.0 |
| VII | Bis(triethanolammonium) salt of ethane-1-hydroxy-1,1-diphosphonic acid | 25.0 |
| VIII | Disodium salt of propane-2,2-diphosphonic acid | 13.0 |
| IX | Diammonium salt of ethane-2-carboxy-1,1-diphosphonic acid | 18.0 |
| X | n-Pentane-1,1-diphosphonic acid | 8.0 |
| XI | Disodium salt of n-nonane-1,1-diphosphonic acid | 24.0 |
| XII | 3-Phenyl-1,1-diphosphonoprop-2-ene | 6.0 |
| XIII | Monoammonium salt of propane-1-hydroxy-1,13-triphosphonic acid | 17.0 |
| XIV | Monomagnesium salt of ethane-2-nydroxy-1,1,3-triphosphonic acid | 23.0 |
| XV | Propane-1,3-diphenyl-2,2-diphosphonic acid | 8.0 |
| XVI | Propane-1,2,3-triphosphonic acid | 25.0 |

The solutions of the foregoing examples when administered by injection to animals (including humans) in an amount sufficient to provide desired dosage levels as hereinbefore specified substantially reduce tissue damage resulting from vascular occlusion or stenosis in organs, including the heart, brain, kidneys, liver, spleen, eyes, as well as the extremeties. Preferably, the solutions are packaged in sealed ampules for single dosage hypodermic injections.

EXAMPLE XVII

A complete feed composition embodying the present invention and useful in the treatment of hypoxic animals, whatever the etiology, is as follows:

| Component | Parts by Weight |
|---|---|
| Timothy hay | 960 |
| Dehydrated alfalfa | 40 |
| Yellow corn | 600 |
| Corn starch | 310 |
| Iodized salt | 10 |
| Bone meal | 20 |
| EHDP (acid form) | 40 |

What is claimed is:

1. A process for increasing the level of 2,3-diphosphoglycerate in the blood of a human or lower animal in need of such treatment, comprising administering to said human or lower animal sufficient organophosphonate compound selected from the group consisting of vicinal organophosphonates of the formula

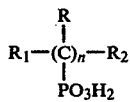

and geminal organophosphonates of the formula

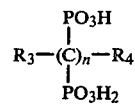

and pharmaceutically acceptable salts thereof, wherein n is an integer from 1 to about 10; R, $R_1$ and $R_2$ are H, —$CH_2OH$, $C_1$–$C_{20}$ alkyl or cycloalkyl, $C_2$–$C_{20}$ alkenyl, aryl, phenylethyl, benzyl, halogen, amino, substituted amino, —$CH_2COOH$, —$CH_2PO_3H_2$, —$CH(PO_3H_2)(OH)$ or —$CH_2CH(PO_3H_2)_2$; $R_3$ is H, $C_1$–$C_{20}$ alkyl or cycloalkyl, $C_2$–$C_{20}$ alkenyl, aryl, phenylethyl, benzyl, halogen, amino, substituted amino, —$CH_2COOH$, —$CH_2PO_3H_2$, —$CH(PO_3H_2)(OH)$ or —$CH_2CH(PO_3H_2)_2$; and $R_4$ is H, lower alkyl, amino, benzyl, halogen, OH, —$CH_2COOH$, —$CH_2PO_3H_2$ or —$CH_2CH_2PO_3H_2$ to increase the blood level of said 2,3-diphosphoglycerate.

2. A process according to claim 1 wherein the organophosphonate compound is a member selected from the group consisting of ethane-1-hydroxy-1,1-diphosphonic acid and the pharmaceutically-acceptable salts and esters thereof.

3. A process according to claim 2 wherein the organophosphonate compound is a sodium salt of ethane-1-hydroxy-1,1-diphosphonic acid.

4. A process according to claim 1 wherein the organophosphonate compound is a member selected from the group consisting of methanediphosphonic acid and the pharmaceutically-acceptable salts and esters thereof.

5. A process according to claim 1 wherein the organophosphonate compound is a member selected from the group consisting of methanedichlorodiphosphonic acid and the pharmaceutically-acceptable salts and esters thereof.